United States Patent [19]

Bell et al.

[11] Patent Number: 4,962,239

[45] Date of Patent: Oct. 9, 1990

[54] PROCESS FOR PREPARING ETHERS

[75] Inventors: Weldon K. Bell, Pennington; Werner O. Haag, Lawrenceville; David O. Marler, Deptford, all of N.J.

[73] Assignee: Mobil Oil Corp., New York, N.Y.

[21] Appl. No.: 456,702

[22] Filed: Dec. 26, 1989

Related U.S. Application Data

[63] Continuation-in-part of Ser. No. 254,524, Oct. 6, 1988, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............................................. C07C 41/05
[52] U.S. Cl. ........................................ 568/697; 502/64
[58] Field of Search .................. 568/697, 699, 698; 502/64

[56] References Cited

U.S. PATENT DOCUMENTS

| | | | |
|---|---|---|---|
| 4,042,633 | 8/1977 | Woods | 260/614 R |
| 4,175,210 | 11/1979 | Selwitz et al. | 568/689 |
| 4,182,914 | 1/1980 | Imaizumi | 568/697 |
| 4,334,890 | 6/1982 | Kochar et al. | 44/53 |
| 4,418,219 | 11/1983 | Hanes et al. | 568/697 |
| 4,439,409 | 3/1984 | Puppe et al. | 423/328 |
| 4,605,787 | 8/1986 | Chu et al. | 568/697 |
| 4,684,757 | 8/1987 | Avidan et al. | 585/314 |
| 4,814,519 | 3/1989 | Harandi et al. | 568/697 |
| 4,820,877 | 4/1989 | Harandi | 568/697 |
| 4,826,667 | 5/1989 | Zones et al. | 423/277 |
| 4,827,046 | 5/1989 | Harandi et al. | 585/310 |
| 4,830,635 | 5/1989 | Harandi et al. | 568/697 |
| 4,835,329 | 5/1989 | Harandi et al. | 568/697 |

FOREIGN PATENT DOCUMENTS

| | | | |
|---|---|---|---|
| 0055045 | 6/1982 | European Pat. Off. | 502/64 |
| 0231860 | 1/1986 | European Pat. Off. | 502/64 |
| 0293032 | 5/1987 | European Pat. Off. | 502/64 |
| 133661 | 1/1977 | Fed. Rep. of Germany | 568/697 |
| 59-25345 | 2/1984 | Japan | 568/697 |

*Primary Examiner*—Anthony McFarlane
*Attorney, Agent, or Firm*—Alexander J. McKillop; Charles J. Speciale; Dennis P. Santini

[57] ABSTRACT

Olefin is etherified with alcohol to provide an ether or mixture of ethers employing catalyst comprising zeolite characterized by an X-ray diffraction pattern including interplanar d-spacings at $12.36 + 0.4$, $11.03 + 0.2$, $8.83 \pm 0.14$, $6.18 \pm 0.12$, $6.00 \pm 0.10$, $4.06 \pm 0.07$, $3.91 \pm 0.07$ and $3.42 \pm 0.06$ Angstroms.

25 Claims, No Drawings

PROCESS FOR PREPARING ETHERS

CROSS-REFERENCE TO RELATED APPLICATIONS

This application is a continuation-in-part of U.S. patent application Ser. No. 254,524, filed Oct. 6, 1988, pending as a continuation-in-part of U.S. patent application Ser. No. 98,176, filed Sep. 18, 1987, which is a continuation-in-part of U.S. patent application Ser. No. 890,268, filed Jul. 29, 1986, both abandoned.

BACKGROUND OF THE INVENTION

This invention relates to a process for the catalytic reaction of olefin(s) with alcohol(s) to provide ether(s). More particularly, the invention relates to a process for the reaction of one or more light olefins such as ethylene, propylene, butene(s), pentene(s), hexene(s), heptene(s), etc., or mixtures thereof, with one or more lower alkanols, e.g., methanol, ethanol, n-propanol, isopropanol, etc., or mixtures thereof, to provide one or more ethers employing the acidic form of a particular synthetic porous crystalline materials, or zeolite, as catalyst. The product ether(s) are useful, inter alia, as high octane blending stocks for gasoline.

Zeolitic materials, both natural and synthetic, have been demonstrated in the past to have catalytic properties for various types of hydrocarbon conversion. Certain zeolitic materials are ordered, porous crystalline aluminosilicates having a definite crysatlline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a varity of ways to take advantage of these properties. Such molecular sieves, both natural and synthetic, include a wide variety of positive ion-containing crystalline silicates. These silicates can be described as a ridid three-dimensional framework of $SiO_4$ and Periodic Table Group IIIA element oxide, e.g., $AlO_4$, in which the tetrahedra are cross-linked by yhr sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crysalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal cotent.

There is a need for an efficient catalytic process to manufacture ethers from the reaction of light olefins with lower alkanols augmenting the supply of high octane blending stocks for gasoline. Relatively low molecular weight eithers such as methyl-t-butyl ether (MTBE) and t-amyl methyl ether (TAME) are in the gasoline boiling range and are known to have a high blending octane number. The petrochemicals industry produces mixtures of light olefin streams in the $C_2$ to $C_7$ molecular weight range and the coversion of such streams or fractions thereof to ethers can also provide products useful as solvents and as blending stocks for gasoline.

The reaction of light olefins with lower alkanols to provide ethers is a known type of process.

According to U.S. Pat. No. 4,042,633, diisopropylether (DIPE) is prepared from isopropyl alcohol (IPA) employing montmorillonite clay catalysts, optionally in the presence of added propylene.

U.S. Pat. No. 4,175,210 discloses the use of silicatungstic acid as catalyst for the reaction of olefin(s) with alcohol(s) to provide ether(s).

As disclosed in U.S. Pat. No. 4,182,914, DIPE is produced from IPA and propylene in a series of operations employing a strongly acidic cation exchange resin as catalyst.

In the process for producing a gasoline blending stock described in U.S. Pat. No. 4,334,890, a mixed $C_4$ steam containing isobutylene is reacted with aqueous ethanol to form a mixture of ethyl tertiary butyl ether and tertiary butanol.

U.S. Pat. No. 4,418,219 describes the preparation of MTBE by reacting isobutylene and methanol in the presence of boron phosphate, blue tungsten oxide or crystalline aluminosilicate zeolite having a silica to alumina mole ratio of at least 12:1 and a constraint index of from 1 to about 12 as catalyst.

U.S. Pat. No. 4,605,787 discloses the preparation of alkyl tert-alkyl ethers such as MTBE and TAME by the reaction of a primary alcohol with an olefin having a double bond on a tertiary carbon atom employing as catalyst an acidic zeolite having a constraint index of from about 1 to 12, e.g., zeolite ZSM-5, -11, -12, -23, dealuminized zeolite Y and rare earth-exchanged zeolite Y.

European Patent Application 55,045 describes a process for reacting an olefin and an alcohol to provide an ether, e.g., isobutene and methanol to provide MTBE, in the presence of an acidic zeolite such as zeolite Beta, zeolites ZSM-5, -8, -11, -12, -23, -35, -43 and -48, and others, as catalyst.

German Patent No. 133,661 describes the reaction of isobutene and methanol to provide a mixture of products including MTBE, butanol and isobutene dimer in the presence of acidic zeolite Y as catalyst.

According to Japanese Patent No. 59-25345, a primary alcohol is reacted with a tertiary olefin in the presence of a zeolite having a silica to alumina mole ratio of at least 10 and the x-ray diffraction disclosed therein to provide a tertiary ether.

SUMMARY OF THE INVENTION

It is an object of this invention to provide a process for manufacturing relatively low molecular weight ether(s) useful as high octane blending stocks for gasoline.

It is a particular object of the invention to provide a process for catalytically reacting olefin(s) with alcohol(s) to provide ether(s) in the presence of catalyst comprising zeolite characterized by an X-ray diffraction pattern including interplanar d-spacings at $12.36\pm0.4$, $11.03\pm0.2$, $8.83\pm0.14$, $6.18\pm0.12$, $6.00\pm0.10$, $4.06\pm0.07$, $3.91\pm0.07$ and $3.42\pm0.06$ Angstroms.

It is a further particular object of this invention to provide a process for manufacturing methyl-t-butyl ether (MTBE) and/or t-amyl methyl ether (TAME) by reacting isobutene and/or isopentene (isoamylene) with methanol in the presence of catalyst comprising zeolite characterized by an X-ray diffraction pattern including interplanar d-spacings at $12.36\pm0.4$, $11.03\pm0.2$, $8.83\pm0.14$, $6.18\pm0.12$, $6.00\pm0.10$, $4.06\pm0.07$, $3.91\pm0.07$ and $3.42\pm0.06$ Angstroms.

By way of realizing the foregoing and other objects of the invention, a process for manufacturing an ether or mixture of ethers is provided which comprises reacting at least one olefin with at least one alcohol under etherification reaction conditions to provide at least one ether employing as catalyst compostion for the etherification reaction, an acidic synthetic porous crystalline material characterized by a X-ray diffraction pattern including values substantially as set forth hereinafter.

The ether, or mixture of ethers, resulting from the foregoing process are advantageously employed as blending components for gasoline or as cosolvents for methanol to be incorporated into gasoline, among other applications.

DESCRIPTION OF SPECIFIC EMBODIMENTS

The entire contents of applications Ser. Nos. 254,524; 98,176; and 890,268 are incorporated herein by reference.

The present invention is applicable to the reaction of individual olefins and mixtures of olefins, preferably within the $C_{3-10}$ range, with individual alcohols and mixtures of alcohols, preferably those possessing up to about 8 carbon atoms and more preferably those possessing from 1 to 4 carbon atoms. Suitable olefins include propylene, butenes, pentenes, hexenes, heptenes, etc., and mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, the following composition is typical for an FCC light olefin stream which can be converted to ethers in accordance with this invention:

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Tertiary olefins are preferred as feedstocks herein with isobutene and/or a tertiary pentene being especially preferred.

Suitable alcohols include lower alkanols such as methanol, ethanol, n-propanol, isopropanol, n-butanol, etc., and substituted lower alkanols, e.g., methoxyethanol, etc. Also contemplated are individual alcohols and mixtures of alcohols which are obtained from the catalytic hydration of olefins in accordance with known and conventional processes. Of the alcohols which are suitable for use herein, the primary and secondary alcohols are preferred with methanol being especially preferred.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| $12.36 \pm 0.4$ | M-VS |
| $11.03 \pm 0.2$ | M-S |
| $8.83 \pm 0.14$ | M-VS |
| $6.18 \pm 0.12$ | M-VS |
| $6.00 \pm 0.10$ | W-M |
| $4.06 \pm 0.07$ | W-S |
| $3.91 \pm 0.07$ | M-VS |
| $3.42 \pm 0.06$ | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| $30.0 \pm 2.2$ | W-M |
| $22.1 \pm 1.3$ | W |
| $12.36 \pm 0.4$ | M-VS |
| $11.03 \pm 0.2$ | M-S |
| $8.83 \pm 0.14$ | M-VS |
| $6.18 \pm 0.12$ | M-VS |
| $6.00 \pm 0.10$ | W-M |
| $4.06 \pm 0.07$ | W-S |
| $3.91 \pm 0.07$ | M-VS |
| $3.42 \pm 0.06$ | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| $12.36 \pm 0.4$ | M-VS |
| $11.03 \pm 0.2$ | M-S |

TABLE C-continued

| Interplanar d-Spacing (A) | Relative Intensity, $I/I_o \times 100$ |
| --- | --- |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensites, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

| W | = | 0-20 |
| --- | --- | --- |
| M | = | 20-40 |
| S | = | 40-60 |
| VS | = | 60-100 |

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 compositon of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10 usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, by used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for the present process. These include hydrogen, rare earth metals and metals of Groups IIA, IIIA, IVA, IB, IIB, IIIB, IVB, and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use as etherification catalyst, the MCM-22 crystals should be subjected to thermal treatment to remove part or all of any organic constituent present therein.

The zeolite etherification catalyst herein can also be used in intimate combination with another having etherification catalystic activity, e.g., any of the known catalysts referred to above.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the etherification process of this invention, the zeolite crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of tempeatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudata having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite crystalline material with another material which is resistant to the temperatures and other conditions employed in the etherification process of this invention. Such materials include active and inactive materials and synthetic or naturally occurring zeolites as wll as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that ether products can be obtained economically and orderly without employing other means for controlling the rate of reaction. These materials may be incorporated into naturally occurring clays, e.g., bentonite and kaolin, to improve the crush strength of the catalyst under commercial etherification operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush stength of the catalyst.

Naturally occurring clays which can be composited with the zeolite crystals include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the zeolite crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the etherification catalyst of the invention may be increased by steaming which is conveniently effected by contacting the zeolite with, for example, 5–100% steam at a temperature of at least 300° C. (e.g. 300°–650° C.) for at least one hour (e.g. 1–200 hours) at a pressure of 110–2,500 kPa. In a more particular embodiment, the catalyst can be made to undergo steaming with 75–100% steam at 315°–500° C. and atmospheric pressure for 2–25 hours.

The operating conditions of the etherification process herein are not especially critical and can include a temperature of from about 20 to about 200° C., preferably from about 50° to about 160° C. and most preferably from about 60° to about 120° C., a total system pressure of from about 2 to about 200 atmospheres, preferably from about 3 to about 80 atmospheres and most preferably from about 10 to about 15 atmospheres and an alcohol to olefin mole ratio of from about 0.1 to about 5, preferably from about 0.2 to about 2 and most preferably from about 0.5 to about 1.2.

The etherification process of this invention can be carried out under liquid phase, vapor phase or mixed vapor-liquid phase conditions in batch or continuous manner using a stirred tank reactor or fixed bed flow reactor, e.g., trickle-bed, liquid-up-flow, liquid-downflow, counter-current, co-current, etc. Reaction times of from about 20 minutes to about 20 hours when operating in batch and an WHSV (gram-olefin per hour gram zeolite) of from about 0.1 to about 200 hour$^{-1}$, preferably from about 0.5 to about 50 hr$^{-1}$ and most preferably from about 1 to about 30 hr$^{-1}$, when operating continuously are suitable. It is generally preferably to recover any unreacted olefin and/or alcohol and recycle same to the reactor.

In order to more fully illustrate the etherification process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure kept constant (within about ±0.5 mm Hg) by addition of adsorbate vapor controlled by a manostat during the adsorption period, which did not exceed about 8 hours. As adsorbate was adsorbed by the cystalline material, the decrease in pressure caused the manostate to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec $^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | | |
|---|---|---|
| $SiO_2/Al_2O_3$ | = | 30.0 |
| $OH^-/SiO_2$ | = | 0.18 |
| $H_2O/SiO_2$ | = | 44.9 |
| $Na/SiO_2$ | = | 0.18 |
| $R/SiO_2$ | = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |

-continued

| | |
|---|---|
| n-Hexane | 16.7 wt. % |

The surface area of the calcined crystalline material was measured to be 494 m²/g.

The chemical composition of the uncalcined material was determined to be as follows:

| Component | wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio | 21.1 |

TABLE E

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were analyzed by X-ray diffraction, sorption, surface area and chemical analyses and the results are presented in Table F. The sorption and surface area measurements were of the calcined product.

TABLE F

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m²/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results are set forth in Table G:

TABLE G

| Product Composition uncalcined | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption wt. % | |
| Cyclohexane | 9.1 |
| N-Hexane | 14.9 |
| H$_2$O | 16.8 |
| Surface Area, m²/g | 479 |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Ionic Composition, wt. % | Exchange Ions | | |
|---|---|---|---|
| | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3$ | 6.1 |
| $OH^-/SiO_2$ | 0.06 |
| $H_2O/SiO_2$ | 19.0 |
| $K/SiO_2$ | 0.06 |
| $R/SiO_2$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the uncalcined crystalline material was measured (BET) to be 405 m²/g.

The chemical composition of the calcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3$ | 12.3 |
| $OH^-/SiO_2$ | 0.056 |
| $H_2O/SiO_2$ | 18.6 |
| $K/SiO_2$ | 0.056 |
| $R/SiO_2$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438 m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLES 15-43

These examples compare the etherification catalyst performance for three zeolites: ZSM-5 of about 70:1 $SiO_2/Al_2O_3$ mole ratio (Examples 15 to 25), USY of about 6:1 $SiO_2/Al_2O_3$ mole ratio (Examples 26 to 33) and MCM-22 of about 26:1 $SiO_2/Al_2O_3$ mole ratio (Examples 34 to 43). The MCM-22 catalyst was prepared as above, specifically by adding 4.49 parts of hexamethyleneimine to a mixture containing 1.00 part sodium aluminate, 1.00 part 50% NaOH, 8.54 parts Ultrasil VN3 and 44.19 parts deionized H$_2$O. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized H$_2$O and dried. A portion of the zeolite crystals was combined with Al$_2$O$_3$ to form a mixture of 65 parts, by weight, zeolite and 35 parts Al$_2$O$_3$. Water was added to this mixture to allow the resulting catalyst to be formed into extrudates. The catalyst was activated by calcining in nitrogen at 540° C. (1000° F.) for six hours, followed by aqueous ammonium nitrate exchange and calcining in air at 540° C. (1000° F.) for six hours.

In all examples, methanol and either isobutene or isoamylene (isopentene) were introduced at various space velocities ranging from 2 to 200 into an up-flow fixed bed reactor charged with one of the foregoing zeolite catalysts diluted to about 10% (vol.) in sand to constant volume.

The reaction conditions and results for these examples are set forth in Tables H, I and J as follows:

TABLE H

| | ZSM-5 ETHERIFICATION CATALYST | | | | | | | | | | |
|---|---|---|---|---|---|---|---|---|---|---|---|
| Example | 15 | 16 | 17 | 18 | 19 | 20 | 21 | 22 | 23 | 24 | 25 |
| Conversion Conditions | | ←isobutene→ | | | | | | ←isopentene→ | | | |
| Hrs on Stream | 18 | 22 | 24 | 43 | 145 | 162 | 163 | 165 | 168 | 187 | 193 |
| Temp., °C. | 99 | 102 | 100 | 98 | 101 | 100 | 101 | 100 | 100 | 99 | 100 |
| Pressure, psi | 205 | 205 | 205 | 205 | 207 | 205 | 208 | 206 | 205 | 205 | 205 |
| Mole Ratio MeOH/Olefin | 2.03 | 1.95 | 2.03 | 1.86 | 2.02 | 1.68 | 1.99 | 2.11 | 1.87 | 2.04 | 2.21 |
| WHSV (olefin) | 5.94 | 26.12 | 12.24 | 3.06 | 31.91 | 3.37 | 64.20 | 15.33 | 7.71 | 1.90 | 3.37 |
| % Conversion Based on Products | | | | | | | | | | | |
| Methanol | 42.0 | 23.9 | 34.1 | 45.2 | 1.7 | 17.1 | 1.0 | 2.9 | 8.2 | 19.9 | 15.1 |
| Isobutene | 80.3 | 47.6 | 64.7 | 83.6 | 0.0 | 0.0 | 0.0 | 0.0 | 0.0 | 0.0 | 0.0 |
| Isopentene | 0.0 | 0.0 | 0.0 | 0.0 | 2.4 | 22.6 | 1.3 | 4.3 | 12.3 | 31.5 | 26.0 |
| Product Composition, Wt. % | | | | | | | | | | | |
| MTBE | 99.86 | 99.87 | 99.89 | 99.92 | 0.00 | 0.00 | 0.00 | 0.00 | 0.00 | 0.00 | 0.00 |
| TAME | 0.00 | 0.00 | 0.00 | 0.00 | 100.00 | 100.00 | 100.00 | 100.00 | 100.00 | 99.32 | 100.00 |
| Hydrocarbons | 0.14 | 0.13 | 0.11 | 0.08 | 0.00 | 0.00 | 0.00 | 0.00 | 0.00 | 0.68 | 0.00 |

TABLE I

| | USY ETHERIFICATION CATALYST | | | | | | | |
|---|---|---|---|---|---|---|---|---|
| Example | 26 | 27 | 28 | 29 | 30 | 31 | 32 | 33 |
| Conversion Conditions | | ←isobutene→ | | | | ←isopentene→ | | |
| Hrs on Stream | 3 | 5 | 22 | 1 | 3 | 4 | 21 | 23 |
| Temp., °C. | 100 | 101 | 101 | 102 | 101 | 101 | 101 | 101 |
| Pressure, psi | 205 | 205 | 210 | 205 | 205 | 205 | 205 | 205 |
| Mole Ratio MeOH/Olefin | 2.02 | 2.02 | 1.94 | 2.00 | 1.91 | 1.99 | 2.04 | 2.01 |
| WHSV (olefin) | 204.96 | 102.36 | 46.92 | 299.98 | 200.20 | 95.62 | 51.74 | 96.92 |
| % Conversion Based on Products | | | | | | | | |
| Methanol | 0.2 | 0.3 | 0.5 | 0.1 | 0.1 | 0.1 | 0.3 | 0.1 |
| Isobutene | 0.4 | 0.7 | 1.1 | 0.0 | 0.0 | 0.0 | 0.0 | 0.0 |
| Isopentene | 0.0 | 0.0 | 0.0 | 0.2 | 0.2 | 0.2 | 0.5 | 0.2 |
| Product Composition, Wt. % | | | | | | | | |
| MTBE | 97.39 | 97.29 | 98.02 | 0.00 | 0.00 | 0.00 | 0.00 | 0.00 |
| TAME | 0.00 | 0.00 | 0.00 | 0.00 | 100.00 | 100.00 | 100.00 | 100.00 |
| Hydrocarbons | 2.61 | 2.71 | 1.98 | 0.00 | 0.00 | 0.00 | 0.00 | 0.00 |

TABLE J

| | MCM-22 ETHERIFICATION CATALYST | | | | | | | | | |
|---|---|---|---|---|---|---|---|---|---|---|
| Example | 34 | 35 | 36 | 37 | 38 | 39 | 40 | 41 | 42 | 43 |
| Conversion Conditions | | ←isobutene→ | | | | | | ←isopentene→ | | |
| Hrs on Stream | 2 | 4 | 21 | 24 | 27 | 48 | 82 | 53 | 69 | 72 |
| Temp., °C. | 101 | 100 | 100 | 100 | 100 | 100 | 100 | 100 | 100 | 100 |
| Pressure, PSI | 200 | 200 | 200 | 200 | 200 | 240 | 210 | 210 | 210 | 210 |
| Mole Ratio MeOH/Olefin | 1.99 | 2.53 | 2.61 | 1.96 | 1.98 | 2.04 | 1.89 | 2.01 | 1.96 | 1.99 |
| WHSV (olefin) | 16.56 | 28.87 | 4.19 | 34.20 | 8.29 | 4.13 | 8.80 | 21.01 | 5.40 | 10.14 |
| % Conversion Based on Products | | | | | | | | | | |
| Methanol | 8.4 | 9.8 | 17.2 | 11.7 | 19.9 | 26.2 | 25.9 | 2.6 | 13.4 | 13.2 |
| Isobutene | 44.9 | 33.5 | 66.4 | 36.3 | 69.7 | 72.9 | 50.1 | 0.0 | 0.0 | 0.0 |
| Isopentene | 0.0 | 0.0 | 0.0 | 0.0 | 0.0 | 0.0 | 0.0 | 13.0 | 26.4 | 25.0 |
| Product Composition, Wt. % | | | | | | | | | | |
| MTBE | 97.06 | 96.54 | 97.15 | 95.61 | 95.60 | 96.62 | 96.24 | 0.00 | 0.00 | 0.00 |
| TAME | 0.00 | 0.00 | 0.00 | 0.00 | 0.00 | 0.00 | 0.00 | 100.00 | 99.64 | 99.53 |
| Hydrocarbons | 2.94 | 3.46 | 2.85 | 4.39 | 4.40 | 3.38 | 3.76 | 0.00 | 0.36 | 0.47 |

The activities of the three etherification catalysts compared in Examples 15—43 were quantified using the following rate law:

$$\ln\left(1 - \frac{X}{X_{eq}}\right) = -\frac{k}{X_{eq}} \frac{s.26}{WHSV} \frac{1}{}$$

where k is the pseudo first order rate constant, X is the olefin conversion, and $X_{eq}$, the value of conversion at equilibrium has experimental values of 93% for isobutene and 51% for isoamylene for the foregoing etherification reaction conditions. Comparison of the kinetics of etherification for the three zeolite catalysts are set forth in Table K as follows:

TABLE K

Etherification Kinetics For Zeolite Catalysts

| Examples | Zeolite Catalyst | Rate Constant Mole/Hr Gm Cat. MTBE | TAME | Performance Ratio (PR) $\frac{TAME}{MTBE} \times 100$ |
|---|---|---|---|---|
| 15-25 | ZSM-5 | 0.21 | 0.014 | 6.7 |
| 26-33 | USY | 0.01 | 0.003 | 30 |
| 34-43 | MCM-22 | 0.16 | 0.032 | 20 |

In Table K, Performance Ratio (PR) quantifies the rate at which isoamylene is consumed by methanol relative to the rate for isobutene. In a mixed feed process, it is generally desirable that this ratio be at least 10 and preferably greater than 15. A ratio of 100 indicates that olefins of both low and high carbon numbers will tend to be consumed at comparable rates. Of the three zeolite catalysts, USY has the better TAME/MTBE PR. However, the rate constants for USY show that this catalyst has a very low activity. Both MCM-22 and ZSM-5 have acceptably higher activity. However, in contrast, MCM-22 has the superior combination of good activity with desirable selectivity as shown by its PR.

EXAMPLES 44–46

These examples illustrate the preparation of ethyl tertiary-butyl ether (ETBE) which is useful, among other applications, as a high octane blending stock for gasoline, employing as catalyst, 65 wt. % MCM-22 in 35 wt. % alumina (binder) in accordance with this invention.

The conditions under which ethanol ws reacted with isobutene in each example and the results obtained are set forth in Table L as follows:

TABLE L

Reaction of Isobutylene With Ethanol Over MCM-22 Etherification Catalyst to Provide ETBE

| | Example | | |
|---|---|---|---|
| | 44 | 45 | 46 |
| Conversion Conditions | | | |
| Hrs. on Stream | 2 | 3 | 5 |
| Temp. °C. | 100 | 101 | 101 |
| Pressure, psi | 200 | 210 | 210 |
| Mole Ratio E + OH/Olefin | 1.98 | 1.98 | 2.05 |
| WHSV (olefin) | 5.91 | 5.91 | 12.24 |
| % Conversion Based on Products | | | |
| Ethanol | 5.0 | 8.1 | 3.7 |
| Isobutene | 12.1 | 17.4 | 7.0 |
| Product Composition, Wt. % | | | |
| Isobutene | 29 | 30 | 36 |
| Ethanol | 63 | 59 | 59 |
| ETBE | 7 | 12 | 5 |
| Other* | <0.5 | <0.5 | <0.5 |

*These other materials may have been impurities in the feed.

What is claimed is:

1. A process for manufacturing an ether or mixture of ethers which comprises reacting at least one olefin with at least one alcohol under etherification reaction conditions to provide at least one ether employing an etherification catalyst composition comprising an acidic synthetic porous crystalline material characterized by an X-ray diffraction pattern including values substantially as set forth in Table A of the specification.

2. The process of claim 1 wherein the synthetic porous crystalline material is characterized by an X-ray diffraction pattern including values substantially as set forth in Table B of the specification.

3. The process of claim 1 wherein the synthetic porous crystalline material is characterized by an X-ray diffraction pattern including values substantially as set forth in Table C of the specification.

4. The process of claim 1 wherein the synthetic porous crystalline material is characterized by an X-ray diffraction pattern including values substantially as set forth in Table D of the specification.

5. The process of claim 1 wherein the synthetic porous crystalline material has a composition comprising the molar relationship $$X_2O_3: (n)YO_2,$$

wherein n is at least about 10, X is a trivalent element and Y is a tetravalent element.

6. The process of claim 1 wherein the synthetic porous crystalline material possesses equilibrium adsorption capacities of greater than about 4.5 wt. % for cyclohexane vapor and greater than about 10 wt. % for n-hexane vapor.

7. The process of claim 5 wherein X is selected from the group consisting of aluminum, boron, gallium and combinations thereof and Y is selected from the group consisting of silicon, germanium and combinations thereof.

8. The process of claim 5 wherein X comprises aluminum and Y comprises silicon.

9. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

10. The process of claim 1 wherein said synthetic porous crystalline material has been thermally treated at a temperature up to about 925° C. in the presence or absence of steam.

11. The process of claim 9 wherein said synthetic porous crystalline material has been thermally treated at a temperature up to about 925° C. in the presence or absence of steam.

12. The process of claim 1 wherein the olefin possesses 3 to 10 carbon atoms.

13. The process of claim 12 wherein the olefin is one or a mixture of propylene, one or more butenes, one or more pentenes, one or more hexenes or one or more heptenes.

14. The process of claim 12 wherein the olefin is a tertiary olefin.

15. The process of claim 14 wherein the tertiary olefin is an isobutene or isopentene.

16. The process of claim 1 wherein the alcohol possesses up to 8 carbon atoms.

17. The process of claim 16 wherein the alcohol is a primary or secondary alkanol.

18. The process of claim 16 wherein the alcohol is methanol, ethanol, n-propanol, isopropanol or a butanol or a mixture of any of the foregoing.

19. The process of claim 14 wherein the alcohol is methanol, ethanol, n-propanol, isopropanol or a butanol or mixture of any of the foregoing.

20. The process of claim 14 wherein the tertiary olefin is isobutene and the alcohol is methanol.

21. The process of claim 14 wherein the tertiary olefin is isobutene and the alcohol is ethanol.

22. The process of claim 14 wherein the tertiary olefin is isopentene and the alcohol is methanol.

23. The process of claim 14 wherein the tertiary olefin is isopentene and the alcohol is ethanol.

24. The process of claim 14 wherein the tertiary olefin is isobutene and the alcohol is isopropanol.

25. The process of claim 1 wherein the etherification reaction conditions include a temperature of from about 20° to about 200° C., a total system pressure of from about 1 to about 200 atmospheres, an alcohol to olefin mole ratio of from about 0.1 to about 5 and a WHSV of from 0.1 to about 200 hr$^{-1}$.

* * * * *

UNITED STATES PATENT AND TRADEMARK OFFICE
CERTIFICATE OF CORRECTION

PATENT NO. : 4,962,239
DATED : 10/9/90
INVENTOR(S) : W.K. Bell et al

It is certified that error appears in the above-identified patent and that said Letters Patent is hereby corrected as shown below:

Col. 1, line 39, "varity" should be --variety--
Col. 1, line 43, "ridid" should be --rigid--
Col. 1, line 46, "yhr" should be --the--
Col. 2, line 21, "cotent" should be --content--
Col. 3, line 44, "compostion" should be --composition--
Col. 8, line 30, "extrudata" should be --extrudate--
Col. 9, line 38, "2" should be --1--
Col. 10, line 4, insert --was-- before "kept"
Col. 13, line 57, "uncalcined" should be --calcined--
Col. 13, line 59, "calcined" should be --uncalcined--
Col. 16, line 66, delete "s,26"

Signed and Sealed this

Fourth Day of February, 1992

*Attest:*

HARRY F. MANBECK, JR.

*Attesting Officer*  *Commissioner of Patents and Trademarks*